US00PP08330P

United States Patent [19]

VandenBerg

[11] Patent Number: Plant 8,330

[45] Date of Patent: Jul. 27, 1993

[54] CHRYSANTHEMUM PLANT NAMED YELLOW DANA

[75] Inventor: Cornelis P. VandenBerg, Salinas, Calif.

[73] Assignee: Yoder Brothers, Inc., Barberton, Ohio

[21] Appl. No.: 743,096

[22] Filed: Aug. 9, 1991

[51] Int. Cl.[5] ..... A01H 5/00

[52] U.S. Cl. ..... Plt./82.2

[58] Field of Search ..... Plt./82.1, 82.2

[56] References Cited

U.S. PATENT DOCUMENTS

| | | | |
|---|---|---|---|
| P.P. 6,399 | 11/1988 | Duffett et al. | Plt. 82.1 |
| P.P. 6,881 | 6/1989 | VandenBerg | Plt. 82.1 |
| P.P. 6,943 | 7/1989 | VandenBerg | Plt. 82.2 |
| P.P. 6,954 | 7/1989 | VandenBerg | Plt. 82.2 |
| P.P. 7,511 | 4/1991 | VandenBerg | Plt. 82.2 |
| P.P. 7,600 | 7/1991 | VandenBerg | Plt. 82.2 |
| P.P. 7,673 | 10/1991 | VandenBerg | Plt. 82.2 |
| 4,616,099 | 10/1986 | Sparkes | 47/58 |

OTHER PUBLICATIONS

Gosling, ed., 1979, "The Chrysanthemum Manual-6th edition", The National Chrysanthemum Society, London, Essex Telegraph Press, Ltd, pp. 329-336.

Broertjes, et al., 1978, "Application of Mutation Breeding Methods in the Improvement of Vegetatively Propagated Crops", Elsevier Sci. Pub. Co., New York, pp. 162-175.

Broertjes, et al., 1980, "A mutant of a mutant of a . . . Irradiation of progressive radiation-induced mutants in a mutation breeding programme with *C. morifulium*", Euphytica, 29:526-530.

Searle, et al., 1968, "Chrysanthemums the Year Round", Blanford Press, London, pp. 27-29, 320-327.

Chan, 1966, "Chrysanthemum and rose mutations induced by X-rays", Am. Soc. Hort. Sci. Proc. pp. 613-620.

Broertjes, 1966, "Mutation breeding of Chrysanthemums", Euphytics, 15:156-162.

Dowrick et al., 1966, "The induction of mutations in Chrysanthemum using X-and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Yellow Dana particularly characterized by its flat capitulum form; daisy capitulum type; yellow ray floret color; diameter across face of capitulum of 76 to 80 mm when fully opened, when grown as a pinched spray pot mum; photoperiodic flowering response to short days of 54 to 56 days; plant height, with 15 to 16 long days after sticking unrooted cuttings, and with 1 application of 2500 ppm B-9 SP, ranges from 28 to 30 cm when grown as a pinched pot mum with 4 cuttings in a 15 cm pot; branching pattern is spreading and prolific, each plant having 4 to 5 laterals after pinch; and recommended as spray pot mum.

1 Drawing Sheet

The present invention comprises a new and distinct cultivar of Chrysanthemum, botanically known as *Dendranthema grandiflora,* and referred to by the cultivar name Yellow Dana.

Yellow Dana, identified as 5475 (83-813A29), is a product of a mutation induction program. The new cultivar was discovered and selected by Cornelis P. VandenBerg on Jun. 9, 1989 in a controlled environment in Salinas, Calif., as one flowering plant within a flowering block established as rooted cuttings from stock plants which had been exposed as unrooted cuttings to an X-ray source of 2000 rads in Fort Myers, Fla., on Nov. 10, 1988. The irradiated parent cultivar was the cultivar identified as Dana, disclosed in U.S. Plant Pat. No. 7,243, and described as a daisy spray pot mum with a flat capitulum form; white ray floret color; diameter across face of capitulum of 76 to 83 mm when fully opened; flowering response period of 49 to 57 days after start of short days; plant height of 20 to 30 cm with 1 to 3 applications of 2500 ppm B-9 SP when grown as a pinched pot mum in a 15 cm pot; and spreading and prolific branching pattern, with 4 to 5 laterals after pinch.

The irradiation program resulting in Yellow Dana had as its primary objective the expansion of color ranges of the parent cultivar Dana. The irradiation program comprised irradiating cuttings of the parent cultivar at irradiation levels of 1500, 1750 and 2000 rads.

A total of 1346 cuttings harvested from a total of 225 irradiated plants were planted on Apr. 17, Apr. 17 and Mar. 27, 1989. Of these, 21 initial selections were made, which selections were then revegetated and reflowered. Three consecutive flowerings resulted in discarding 19 of the original 21 selections on Feb. 28, 1990. Two selections were retained and identified as Yellow Dana and Cream Dana. The latter is disclosed in pending application Ser. No. 07/742,901 of applicant, and is similar in characteristics to Yellow Dana except for its cream ray floret color and slightly later (1-2 days) flowering response to short days.

The first act of asexual reproduction of Yellow Dana was accomplished when vegetative cuttings were taken from the initial selection in August 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Dana are firmly fixed and are retained through successive generations of asexual reproduction.

Yellow Dana has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Yellow Dana, which, in combination, distinguish this Chrysanthemum as a new and distinct cultivar:

1. Flat capitulum form.
2. Daisy capitulum form.
3. Yellow ray floret color.
4. Diameter across face of capitulum of 76 to 80 mm when fully opened, when grown as a pinched spray pot mum.
5. Photoperiodic flowering response to short days of 54 to 56 days.
6. Plant height, with 15 to 16 long days after sticking unrooted cuttings, and with 1 application of 2500 ppm B-9 SP, ranges from 28 to 30 cm when grown as a pinched pot mum with 4 cuttings in a 15 cm pot.
7. Branching pattern is spreading, each plant having 4 to 5 laterals after pinch.
8. Recommended as a spray pot mum.

The accompanying photograhpic drawing is a side view of a potted mum of Yellow Dana, with 4 cuttings in a 15 cm pot, with the colors being as nearly true as possible with illustrations of this type. It should be noted that the depicted foliage color is much ligher than the actual foliage color (147A, upper surface) described below.

Of the commercial cultivars known to the inventor, the most similar in comparison to Yellow Dana is the parent cultivar Dana. All traits of Yellow Dana are similar to those of Dana, except for the ray floret color. In one flowering trial it was noted that Yellow Dana had slightly less vigor than Dana. When comparison the description of Yellow Dana with Dana, it is evident that Dana has a wider range for many characteristics than Yellow Dana. The reason for this is that the description of Dana is based on evaluations over a 3 year time period, while the description of Yellow Dana is based on considerably less flowerings in a shorter period of time.

In the following description color references are made to The Royal Horticultural Society Colour Chart. The color values were determined on plant material grown as a pinched spray pot mum in Salinas, Calif. on Apr. 1, 1991.

Classification:

*Botanical.*—*Dendranthema grandiflora* cv. Yellow Dana.

*Commercial.*—Flat daisy spray pot mum.

INFLORESCENCE

A. Capitulum:

*Form.*—Flat.

*Type.*—Daisy.

*Diameter across face.*—76 to 80 mm when fully opened.

B. Corolla of ray florets:

*Color (general tonality from a distance of three meters).*—Yellow.

*Color (upper surface).*—3A to 5A.

*Color (under surface).*—5B to 5C.

*Shape.*—Straight, slightly concave, rounded petal tips.

C. Corolla of disc florets:

*Color (mature).*—13A.

*Color (immature).*—Yellow, overlaid with 144B.

D. Reproductive organs:

*Androecium.*—Present on disc florets only; scant pollen.

*Gynoecium.*—Present on both ray and disc florets.

PLANT

A. General appearance:

*Height.*—28 to 30 cm when grown as a pinched pot mum with 15 to 16 long days prior to start of short days, with 1 application of 2500 ppm B-9 SP.

*Branching pattern.*—Spreading, with 4 to 5 laterals after pinch.

B. Foliage:

*Color (upper surface).*—147A.

*Color (under surface).*—147B.

*Shape.*—Lobed.

I claim:

1. A new and distinct Chrysanthemum plant named Yellow Dana, as described and illustrated.

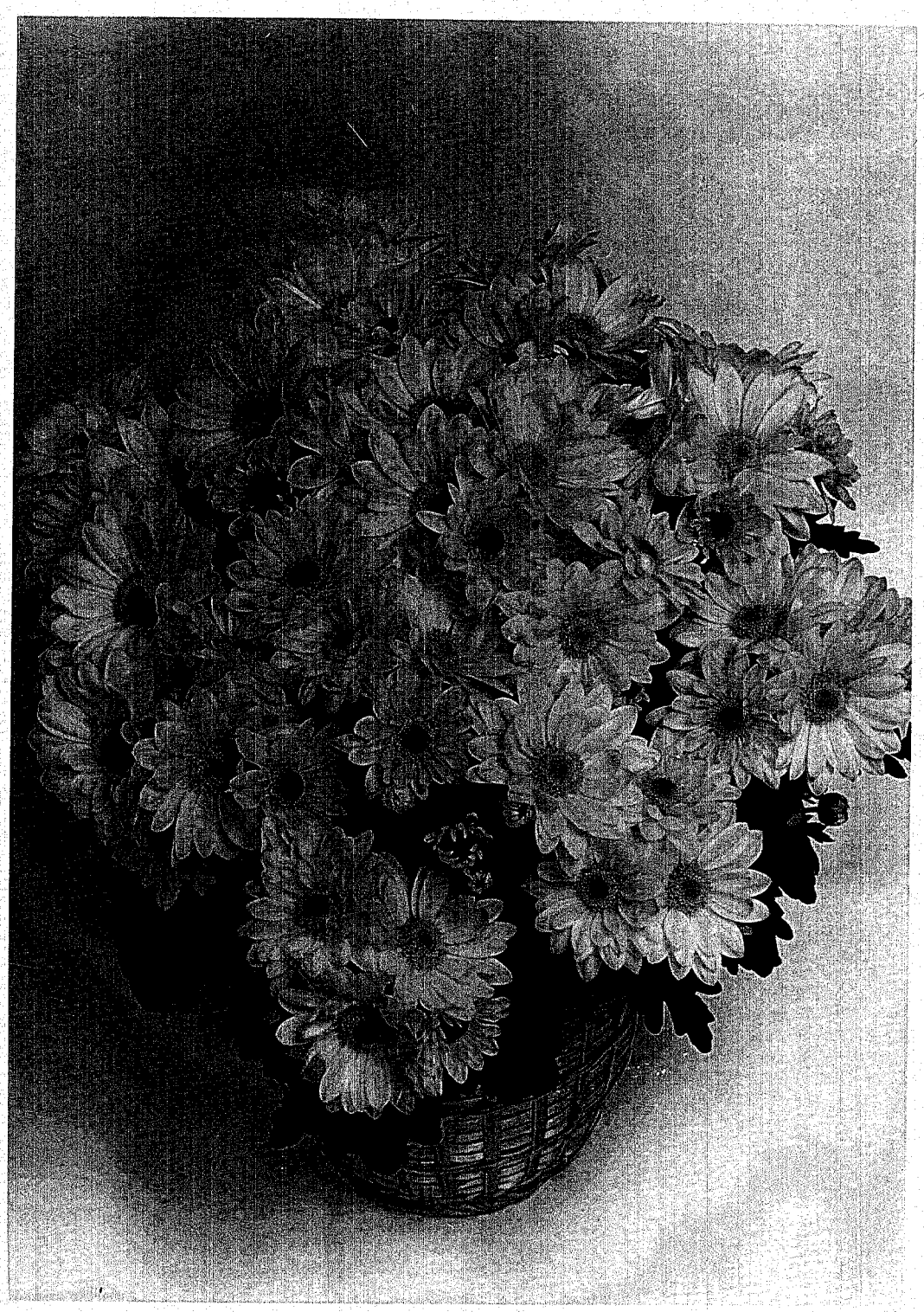

* * * * *